United States Patent
Hemberg et al.

(10) Patent No.: US 11,504,278 B2
(45) Date of Patent: Nov. 22, 2022

(54) ADAPTIVE ELECTRONIC HEARING PROTECTION DEVICE

(71) Applicant: 3M INNOVATIVE PROPERTIES COMPANY, St. Paul, MN (US)

(72) Inventors: Oscar M. Hemberg, Dalarö (SE); Eric O. Hemberg, Shatin (HK); Henrik M. Fransson, Bro (SE); Gregory G. Jager, Oakdale, MN (US); Douglas D. Fletcher, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 902 days.

(21) Appl. No.: 16/337,569

(22) PCT Filed: Sep. 21, 2017

(86) PCT No.: PCT/US2017/052757
§ 371 (c)(1),
(2) Date: Mar. 28, 2019

(87) PCT Pub. No.: WO2018/063917
PCT Pub. Date: Apr. 5, 2018

(65) Prior Publication Data
US 2020/0030151 A1   Jan. 30, 2020

Related U.S. Application Data

(60) Provisional application No. 62/536,741, filed on Jul. 25, 2017, provisional application No. 62/400,819, filed on Sep. 28, 2016.

(51) Int. Cl.
*A61F 11/14*   (2006.01)
*H04R 5/033*   (2006.01)
*H04R 1/10*   (2006.01)

(52) U.S. Cl.
CPC ............ *A61F 11/14* (2013.01); *H04R 1/1008* (2013.01); *H04R 1/1083* (2013.01);
(Continued)

(58) Field of Classification Search
CPC ...... A61F 11/14; A61F 11/145; H04R 1/1008; H04R 1/1083; H04R 5/033; H04R 2410/05; H04R 2430/01; H04R 2460/01
(Continued)

(56) References Cited

U.S. PATENT DOCUMENTS 4,731,850 A   3/1988 Levitt
5,355,418 A   10/1994 Kelsey
(Continued)

FOREIGN PATENT DOCUMENTS

DE   2460535   6/1976
DE   102009004300   7/2010
(Continued)

OTHER PUBLICATIONS

International Search Report for PCT International Application No. PCT/US2017/052757, dated Mar. 21, 2018, 7 pages.

*Primary Examiner* — Vivian C Chin
*Assistant Examiner* — Friedrich Fahnert
(74) *Attorney, Agent, or Firm* — Ann K. Gallagher

(57) ABSTRACT

An electronic hearing protection device is provided. The electronic hearing protection device includes an amplifier and a speaker to relay sounds, such as conversations, to the user of the hearing protection. The hearing protection device provides adaptive gunshot recognition and suppression technology.

19 Claims, 9 Drawing Sheets

(52) U.S. Cl.
CPC ............. *A61F 11/145* (2022.01); *H04R 5/033* (2013.01); *H04R 2410/05* (2013.01); *H04R 2430/01* (2013.01); *H04R 2460/01* (2013.01)

(58) Field of Classification Search
USPC ......................................................... 128/867
See application file for complete search history.

(56) References Cited

U.S. PATENT DOCUMENTS

| | | |
|---|---|---|
| 6,154,547 A | 11/2000 | Whitecar |
| 9,628,897 B2 | 4/2017 | Fletcher |
| 2007/0147628 A1 | 6/2007 | Benway |
| 2008/0253583 A1 | 10/2008 | Goldstein |
| 2009/0296948 A1 | 12/2009 | Hood |
| 2010/0260345 A1 | 10/2010 | Shridhar |
| 2015/0010158 A1 | 1/2015 | Broadley |
| 2015/0117660 A1 | 4/2015 | Fletcher |
| 2015/0370527 A1 | 12/2015 | Goldstein |
| 2016/0076858 A1 | 3/2016 | Howes |
| 2016/0193084 A1 | 7/2016 | Jenkins |

FOREIGN PATENT DOCUMENTS

| | | |
|---|---|---|
| WO | WO 1996-008004 | 3/1996 |
| WO | WO 1999-053612 | 10/1999 |
| WO | WO 2009-029995 | 3/2009 |
| WO | WO 2015-065882 | 5/2015 |
| WO | WO 2016-126476 | 8/2016 |

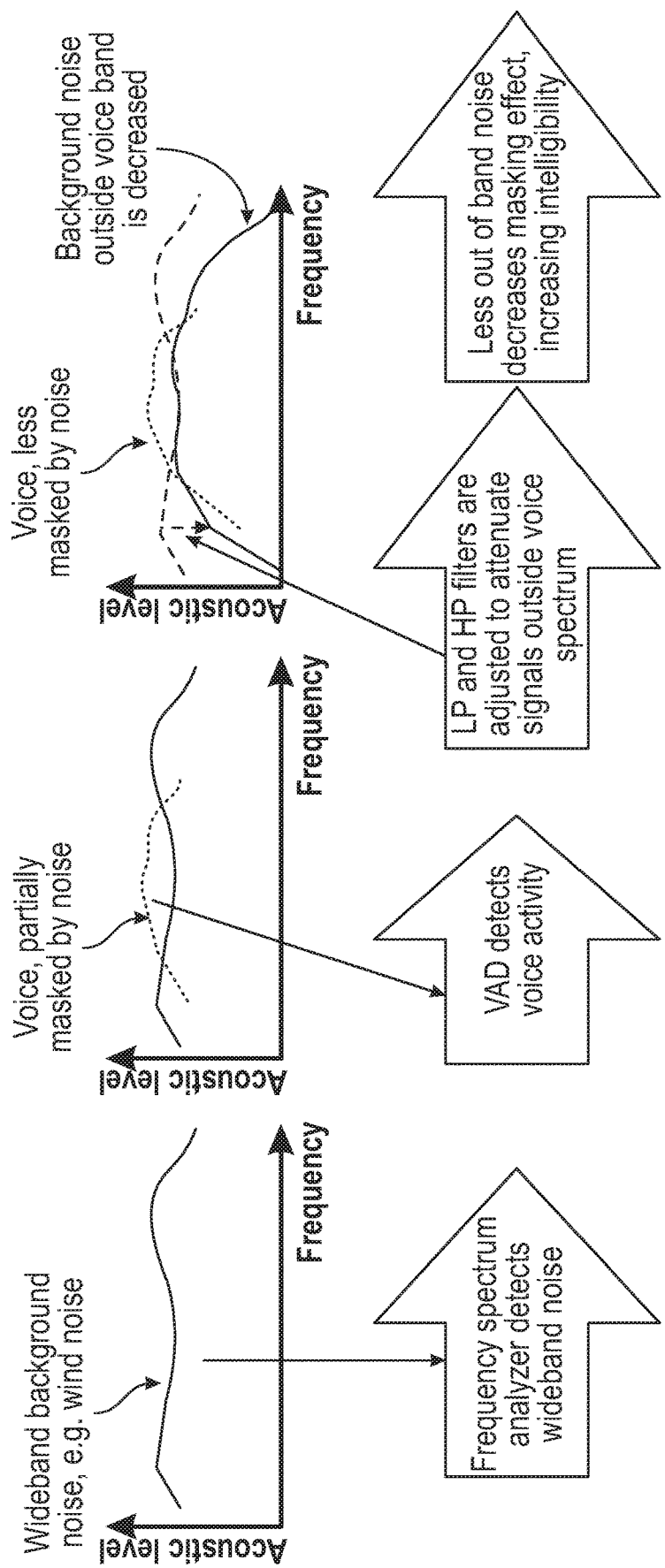

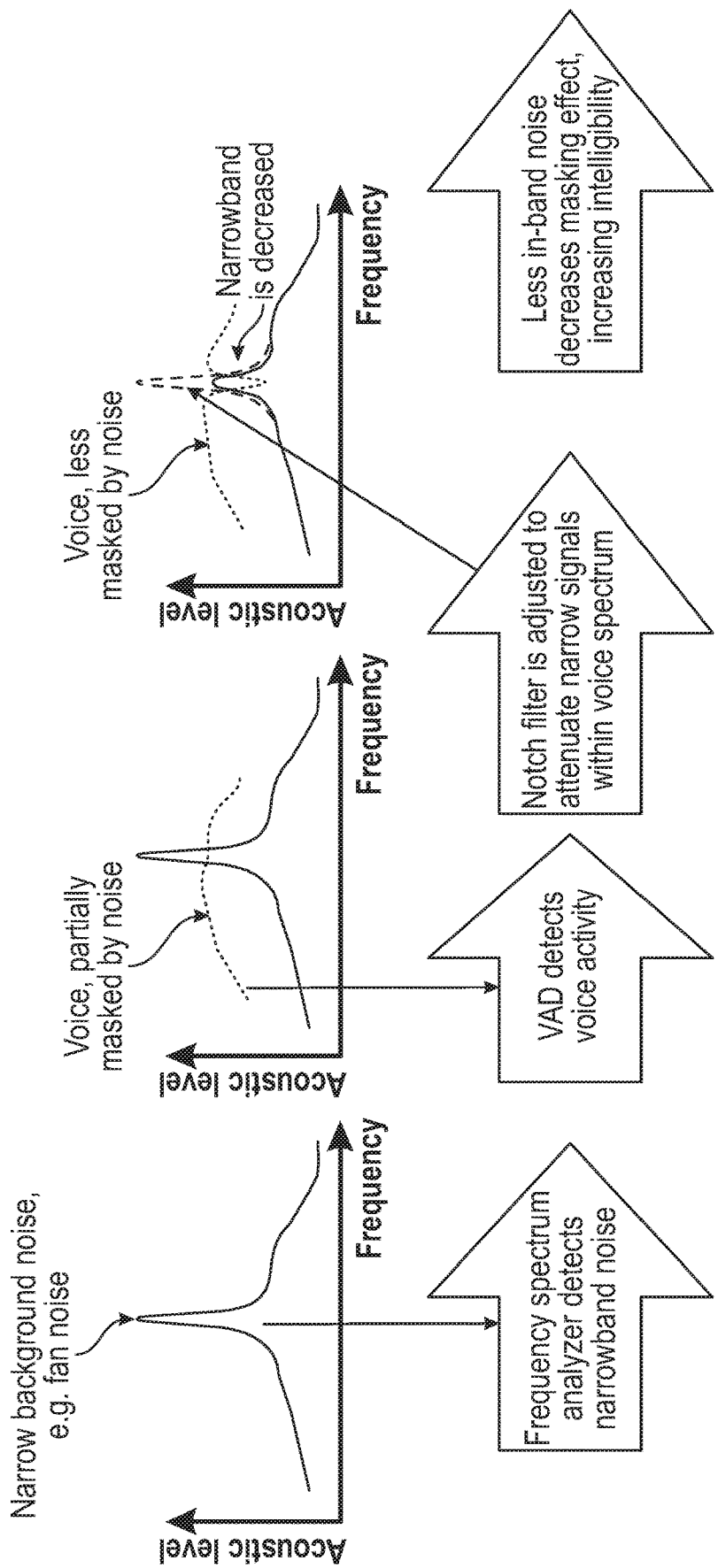

ADAPTIVE ELECTRONIC HEARING PROTECTION DEVICE

CROSS REFERENCE TO RELATED APPLICATIONS

This application is a national stage filing under 35 U.S.C. 371 of PCT/US2017/052757, filed Sep. 21, 2017, which claims the benefit of provisional Application No. 62/536,741, filed Jul. 25, 2017, and provisional Application No. 62/400,819, filed Sep. 28, 2016, the disclosure of which is incorporated by reference in their entirety herein.

BACKGROUND

People frequently wear hearing protection when they are in loud or noisy environments. Hearing protection can reduce the amount of noise the user's ears are exposed to. In some cases the user might want to hear some noises, such as a conversations or commands from people around them, music, other entertainment or other communication (e.g., AM/FM radio transmissions, Bluetooth transmissions, or communication from other transceivers) delivered through an input sound source. If the user is wearing hearing protection, hearing these desirable noises can be difficult or impossible. Therefore, there is a need to allow the user of hearing protection to still be able to hear some external noises, while still reducing the loud or undesirable noises.

Some systems tend to diminish or attenuate more sound than is necessary, which protects the hearing, but the wearer is left out of critical sound information such as noises about her or him, or conversations that contain important information. There is a need to adapt the protection to the sounds experienced by the wearer to provide enhanced protection for relatively large gunshots with increased intelligibility of hearing and comfort for the wearer over the variety of sounds encountered.

SUMMARY

An adaptive hearing protection system is provided. The system includes right and left microphones providing input signals; and a peak detector in communication with an adjustable amplifier to sense high amplitude sounds and attenuate gain of the adjustable amplifier, the peak detector further in communication with a low pass filter that controllably filters signals from the adjustable amplifier, wherein the peak detector includes an adjustable threshold for comparisons of the input signals, the peak detector further configured to provide adjustable attenuation based on input energy of the input signals.

The present disclosure further provides a method for highlighting voice signals in a high noise environment. The method comprises detecting voice signals in a frequency spectrum of interest; detecting a noise level associated with a background noise signal; selecting one or more filters defining a band with a first cutoff frequency and a second cutoff frequency; modifying the width of the band based at least partially on the detected noise level; and attenuating the noise signal below the first cutoff frequency and above the second cutoff frequency.

BRIEF DESCRIPTION OF THE DRAWINGS

FIG. 6A is a graph showing acoustic level versus frequency for wideband background noise in an embodiment.

FIG. 6B is a graph showing acoustic level versus frequency for voice partially masked by noise and wideband background noise according to an embodiment.

FIG. 6C is a graph showing acoustic level versus frequency for signals outside voice spectrum, background noise outside voice band, voice partially masked by noise and wideband background noise, according to an embodiment.

FIG. 7A is a graph showing a graph showing acoustic level versus frequency for narrowband background noise in an embodiment.

FIG. 7B is a graph showing acoustic level versus frequency for voice partially masked by noise and narrowband background noise according to an embodiment.

FIG. 7C is a graph showing acoustic level versus frequency for signals within voice spectrum, background noise, voice less masked by noise and narrowband background noise, according to an embodiment.

While the present disclosure is susceptible to various modifications and alternative forms, specifics thereof have been shown by way of example and drawings, and will be described in detail. It should be understood, however, that the present disclosure is not limited to the particular embodiments described. On the contrary, the intention is to cover modifications, equivalents, and alternatives falling within the spirit and scope of the present disclosure.

DETAILED DESCRIPTION

The embodiments of the present disclosure described herein are not intended to be exhaustive or to limit the present disclosure to the precise forms disclosed in the following detailed description. Rather, the embodiments are chosen and described so that others skilled in the art can appreciate and understand the principles and practices of the present disclosure.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Figure 1:
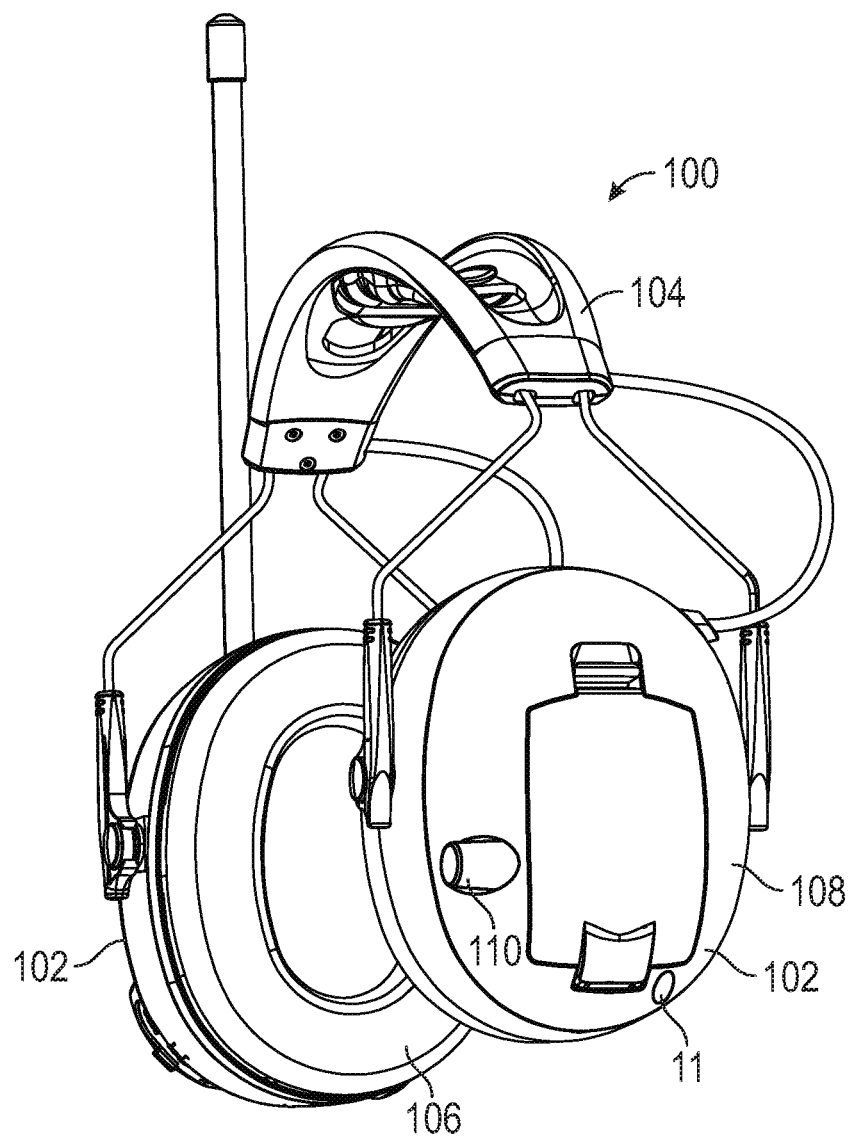
FIG. 1 is a perspective view of a hearing protector, according to an embodiment.

FIG. 1 is a perspective view of a hearing protector 100. In an embodiment, the hearing protector 100 can include an ear cup 102 and a headband 104. The hearing protector 100 can include two ear cups 102. The headband 104 can couple a first ear cup 102 with a second ear cup 102. The headband 104 can be arced, such as to extend over the top of a user's head while the hearing protector 100 is in use. The headband 104 can be flexible, such as to allow the user to spread the first ear cup 102 from the second ear cup 102 when the user is putting on the hearing protector 100. The headband 104 can include padding, such as to at least partially conform to the head and increase the user's comfort.

The ear cups 102 can be configured to fit at least partially around a user's ear, and be disposed on the side of a user's head while in use. The ear cup 102 can define a cavity. The cavity can be configured for a user's ear, a human ear, to fit within the cavity, while the user is wearing the hearing protector 100. The earcup 102 can include a seal ring 106. The seal ring 106 can be ring shaped, such as to extend around the user's ear. The seal ring 106 can be flexible and able to conform to the user's head. The seal ring 106 can provide a seal between the ear cup 102 and the user's head, such as to reduce the amount of noise or sound waves that reach the user's ear, thereby at least partially protecting the user's ear from external noises. The seal ring 106 can include leather, cloth, rubber, plastic, or a polymer, such as polyurethane.

The hearing protector 100 can include a sound input source 108. In one embodiment, one or both of the ear cups 102 can include a sound input source 108. In an embodiment, the sound input source 108 can comprise a microphone. In an embodiment, there is one microphone 108 on each of two ear cups 102. In an embodiment, there can be more than one microphone 108 on one or both of the ear cups 102. In one embodiment, one or more microphones 108 are located at other locations on the hearing protector 100. The microphone 108 can be disposed on the outside surface of the ear cup 102 opposite the cavity. The microphone 108 can pick up sound and noise from the surrounding environment. The microphone 108 can be inset, such that the microphone 108 does not extend past the outer surface of the ear cup 102. In an embodiment with two ear cups 102, each ear cup 102 can include a microphone 108. In another embodiment with two ear cups 102, only one ear cup 102 includes a microphone 108. In another embodiment with two ear cups 102, one microphone 108 is positioned on a headband portion. The noises and sounds picked up by the microphone 108 can be relayed to the user through a speaker in the cavity of the ear cup 102.

One of the ear cups 102 can include a knob 110. The user can rotate the knob 110 to control the electronics of the hearing protector 100, such as to turn the electronics "ON" or "OFF", or to increase or decrease the volume from the speakers in the ear cups 102.

The ear cups 102 can include an input connection 112. The input connection 112 can allow a user to connect an external audio device into the hearing protector 100, such as an AM/FM radio, a two-way radio, an MP3 player, a cellphone, or the like. The user can hear the external audio device through the one or more speakers disposed in the ear cups 102. In an embodiment, the input connection 112 can accommodate a 3.5 mm audio input. In an embodiment, an external audio device can be connected to the hearing protector 100 through a wireless connection, such as Bluetooth connection. In an embodiment, the hearing protector includes a Bluetooth receiver. In an embodiment, the external audio device can be built in or integral with the hearing protector 100.

The ear cups 102 can include a battery compartment. The battery compartment can house one or more batteries or battery packs.

Figure 2:
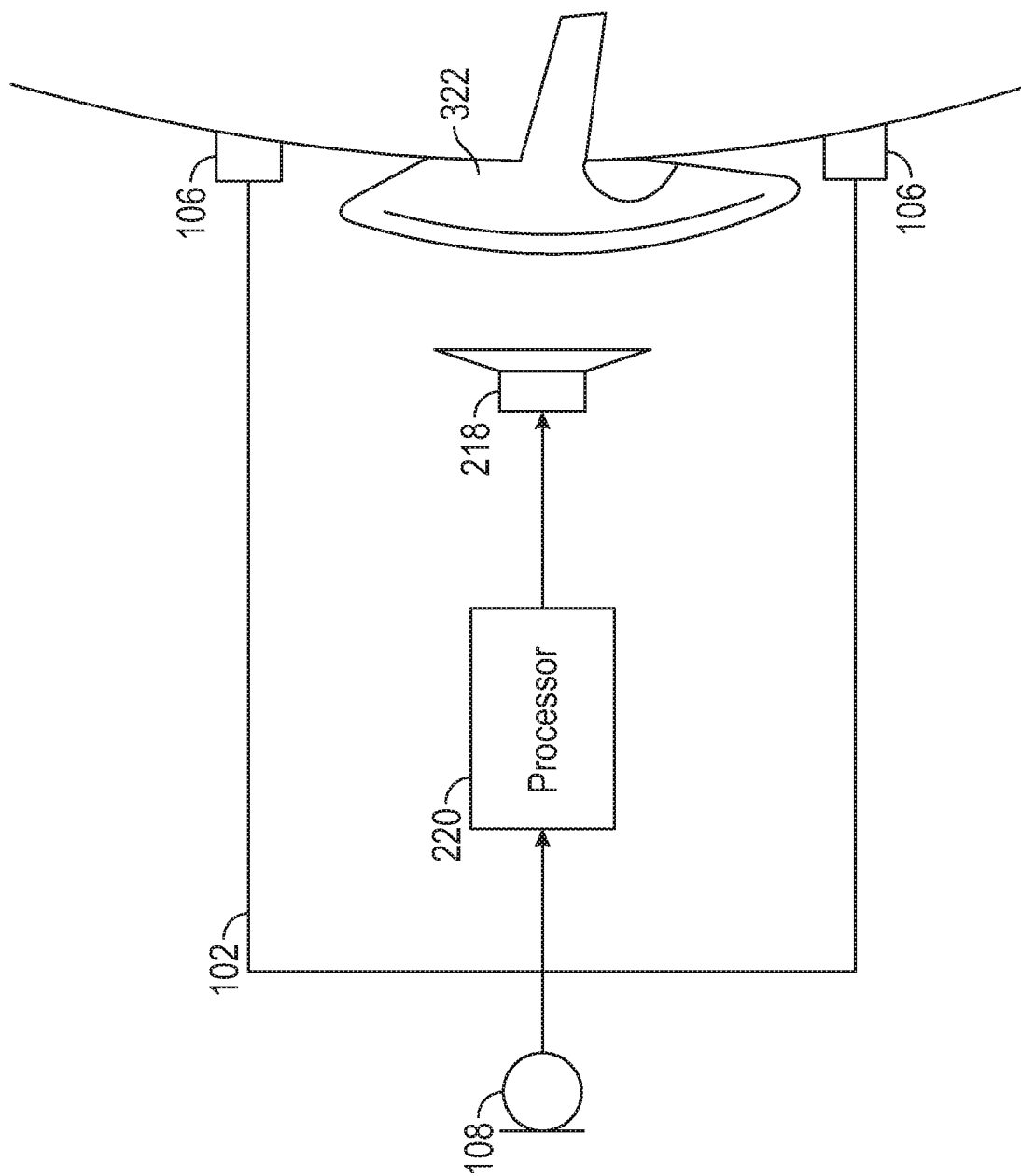
FIG. 2 is a schematic of certain hearing protector components, according to an embodiment.

Each ear cup 102 can include a speaker 218, shown in FIG. 2. The speaker 218 can produce an output, such as a sound wave. Incoming sound and noise from sound input 108 can be input into a processor 220 and be processed, such as to eliminate at least some of the noise, to produce an output through the speaker 218. As used herein, the term sound refers to desirable audio information while the term noise refers to undesirable audio information. The speaker 218 can provide sound to the user, such as desirable audio. Desirable audio can include conversations, commands, warnings or other communications, such as communications between two people. The input from each microphone can be processed to eliminate at least some of the noise, such as undesirable noises. Undesirable noises can include mechanical noises, noises from ventilation systems, distant conversations, impulse noises, grinding, squeaking, engine noises, gun shots, explosions and the other similar noises.

The hearing protector 100 can include digital electronic components, analog electronic components or a mix of both types.

The speaker 218 can relay sounds from the surrounding environment picked up by the sound input 108. The speaker 218 can relay sounds from an external audio device connected from the input connection 108. The output from the speaker 218 can be limited to a maximum output level, such as to protect the user's ears. In different embodiments, the maximum output level from the speaker 218 due to sound from the microphone can be at least 80 dB(A), not more than 90 dB(A), at least 70 dB(A), not more than 100 dB(A), and combinations of these constraints. In an embodiment, the output from the speaker 218 is limited to 82 dB(A) when the ambient sound level is less than 106 dB(A), regardless of how high the user has the volume turned up. In an embodiment, the output from the speaker 218 is limited to 85 dB(A) when the ambient sound level is less than 106 dB(A), regardless of how high the user has the volume turned up. In an embodiment, the output from the speaker 218 is limited to 82 dB(A), regardless of how high the user has the volume turned up. In an embodiment, the output from the speaker 218 is limited to 85 dB(A), regardless of how high the user has the volume turned up. In an embodiment, the output from the speaker 218 can be limited to 82 dB(A) when an external audio device is connected to the input connection 112. The sounds picked up by the microphone 108 can be processed before they are produced as output from the speaker 218. The processing can increase the quality or clarity of what the user hears, such as by reducing background noise, suppressing impulse noises or keeping an input level constant. In one embodiment where each of two ear cups 102 has a microphone 108, the incoming sound and noise is processed by a single processor. In another embodiment where each of the two ear cups 102 has a microphone 108, the incoming sound and noise is processed by separate processors.

The individual features described herein can be present in various embodiments. Also, combinations of the individual features described herein can be present in various embodiments.

Figure 3:
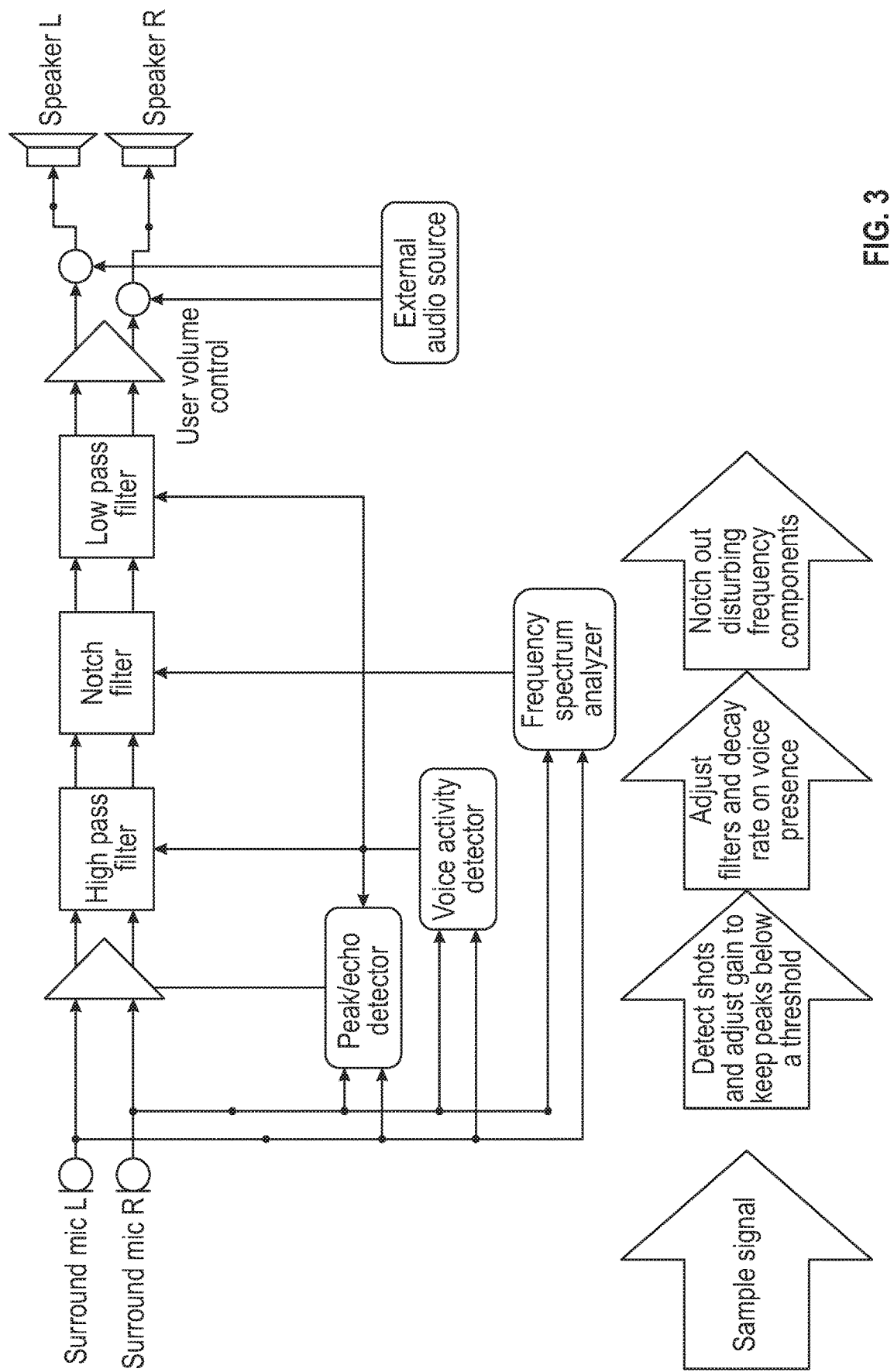
FIG. 3 is a block diagram illustrating signal processing flow according to an embodiment.

FIG. 3 shows a block diagram of an embodiment of a signal processing flow. Microphones 301, 302 disposed at or near the left and right ears of the wearer, shown on the left hand side of FIG. 3, receive sound from the surroundings of the wearer and generate left and right sound signals, respectively. The signal processing circuit 300 processes the signals before playing processed sound to the left and right speakers 303, 304, respectively, on the right hand side of FIG. 3.

In an embodiment, the signal processing circuit includes a peak/echo detection module 310 that adjusts the gain of a signal amplifier 312. The signal processing circuit also includes a voice activity detector (VAD) 314 and filter 316 with adjustable gain based on the output of the VAD. In the embodiment of FIG. 3, filter 316 is one or more high pass filters. The signal processing circuit also includes a frequency spectrum analyzer 318 that optionally adjusts the notch of a notch filter 320. These notch-filtered and/or high-pass filtered signals are subsequently passed through one or more low pass filters 322, which is also in communication with the peak/echo detector 310. The output of these modules is fed through a user volume control 324 and any desired external audio source is added to the resulting audio signal by summing junctions 329 and 330, to form the output signal for speakers 303 and 304, respectively. The signals from the external audio source can be a variety of different sources, including, but not limited to, MP3 compatible signals, Bluetooth™ communications, and two-way radio compatible signals. In various embodiments, a Bluetooth™ interface is used to make and answer telephone calls. In various embodiments, the external audio is supplied using wireless communications, such as Bluetooth™. In various embodiments, the audio is also supplied using an audio input jack. Various combinations of wireless and wired connections and other input signals can be employed in combination without departing from the scope of the present subject matter.

This signal processing approach allows the device to sample the signals, detect shots or other high volume sounds and adjust gain to keep peaks below a threshold level, adjust the decay rate and other parameters for the filters based on voice detection and notch out annoying or disturbing frequency components. The notch filter is especially useful for notching out annoying periodic signals, such as motor noise, etc. A notch filter is not, however, necessary in all embodiments.

The resulting signal processing provides an intelligent and adaptive noise recognition and suppression technology. It is particularly useful for filtering out large noises, such as gunshots and any high amplitude echoes. The signal processing provides improved noise protection, which is a function of the firearms used and the environment, which it works in. It also works to improve overall speech intelligibility by filtering when necessary and as much as necessary to protect the wearer, yet not blank out sound that may be important to the wearer, such as other speech or noises in the environment that occur before and/or after the gunshot (or before and/or after and/or during a series of gunshots or other loud events). The signal processing circuit provides more intelligible clear voice tracking technology.

Figure 4:
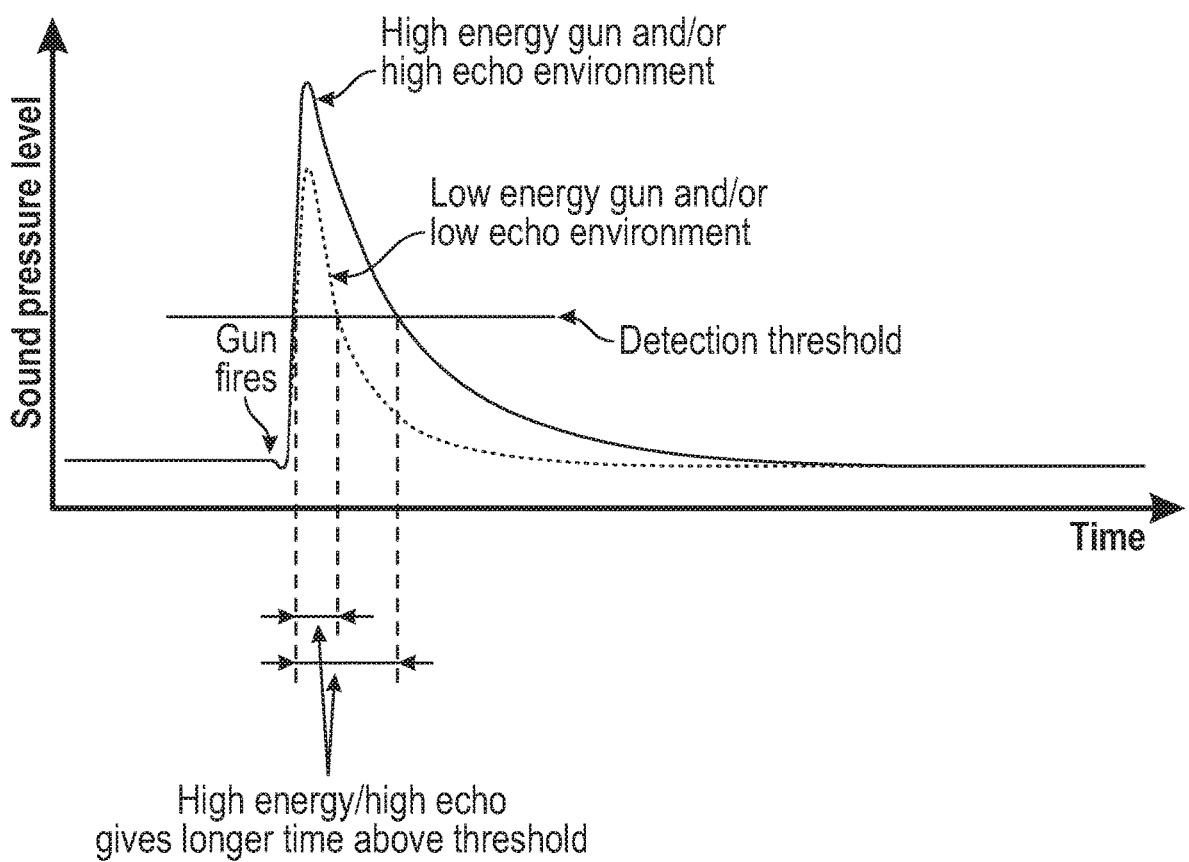
FIG. 4 is a graph showing sound pressure level over time for a high energy gun shot and/or a high echo environment and for a low energy gun shot and/or a low echo environment according to an embodiment.

FIG. 4 shows the adaptive suppression time (AST) based on a gunshot noise energy estimation. The upper trace of FIG. 4 demonstrates that in cases of higher energy gun and/or high echo environments the sound pressure level is higher for a longer duration than in the cases of a lower energy gun and/or low echo environments (lower trace). The amount of attenuation and duration of that attenuation during the gunshot/echo period of interest can be adaptively changed to increase the efficacy of the hearing protection without sacrificing the ability to hear when loud sound is not present. The threshold can be adjusted to enhance hearing protection by lowering the threshold. In the alternative, the threshold can be raised to shorten the duration of time in which attenuation is applied, yet still maintain a safe level of hearing. Accordingly, the present subject matter affords the wearer control over the ultimate tradeoff between sound protection and the ability to listen to desired, safe sounds.

Figure 5:
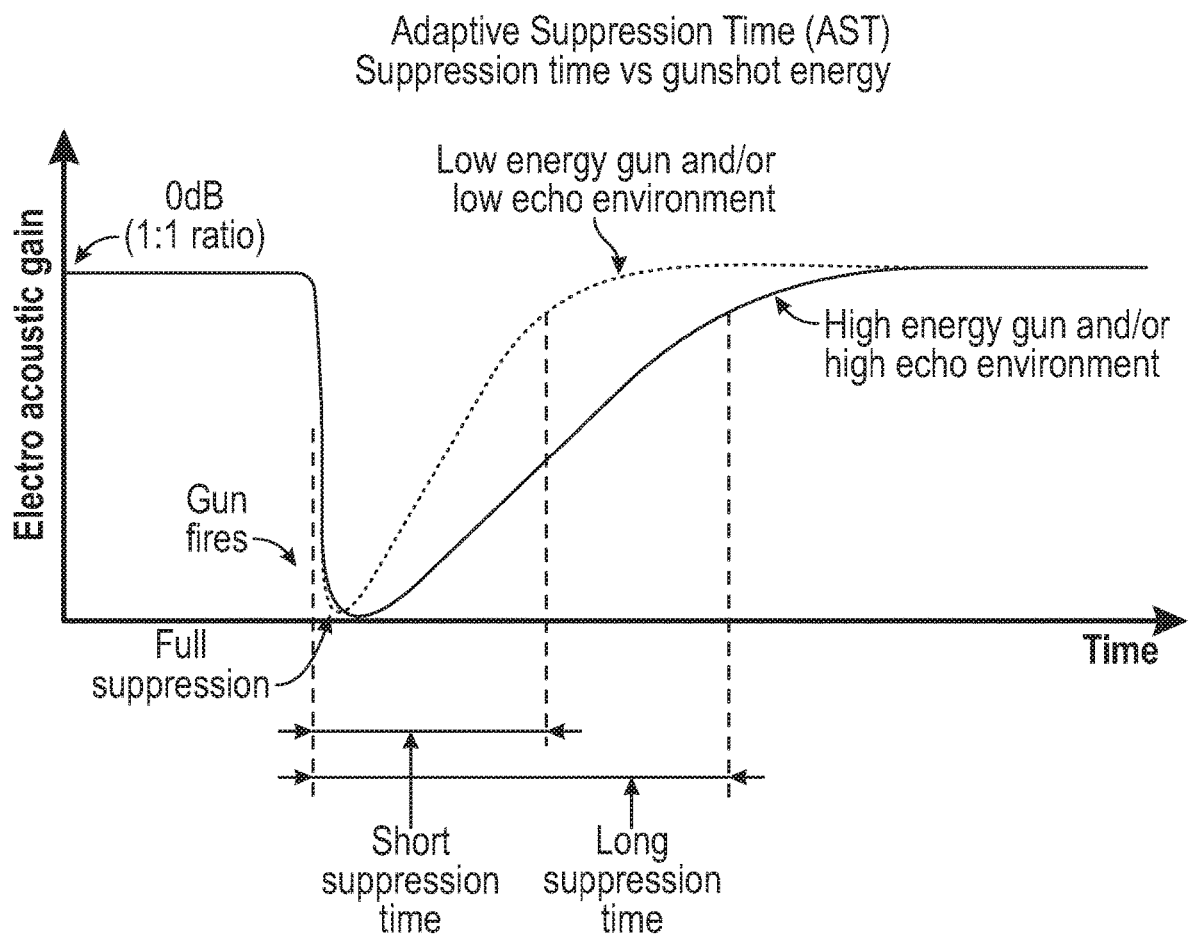
FIG. 5 is a graph showing electro acoustic gain over time for a high energy gun shot and/or a high echo environment and for a low energy gun shot and/or a low echo environment according to an embodiment.

FIG. 5 shows a graph of electro-acoustic gain as a function of the energy level of the gun and/or echoes from the wearer's environment. The signal processing circuit of the embodiments provided herein can provide shorter or longer suppression times based on the energy of the gun/echo sounds of the wearer's environment. Duration and rate of attenuation change can be modified to improve the wearer's comfort, ability to hear desired sounds (particularly voice), while still protecting from unsafe levels.

FIGS. 6A-6C demonstrate the adaptive surround sound filter and how it can be adjusted for desired signals despite noise in the background. FIG. 6A shows wideband noise amplitude as a function of frequency. The wideband noise can represent, for example, outdoor environmental noises (e.g., wind) or continuously operating machinery (e.g., an HVAC system). FIG. 6B shows voice signals, which are partially masked by wideband background noise, yet detectable by the VAD. FIG. 6C demonstrates how the different filters of the system can be adjusted to attenuate signals outside the spectrum of interest, yet pass the voice signals and other signals of interest. In various embodiments, low pass and high pass filters are adjusted to attenuate signals outside of the voice spectrum or other spectrum of interest. The reduction of out-of-band noise makes listening to the desired signal easier and more comfortable for the wearer. This reduction of out-of-band noise also increases intelligibility of the desired input sounds (e.g., speech or other desired sounds) for the wearer.

FIGS. 7A-7C demonstrate the adaptive surround sound filter and how it can be adjusted for desired signals despite narrowband noise in the background. FIG. 7A shows the narrowband background noise amplitude as a function of frequency. The peak represents narrowband noise, which the frequency spectrum analyzer may detect as narrowband noise. FIG. 7B shows voice signals, which are partially masked by the background narrowband noise, yet which are still detectable by the VAD. FIG. 7C demonstrates how the notch filter of the system is adjusted to attenuate narrowband signals within the spectrum of interest (e.g., the voice spectrum). The reduction of unwanted narrowband noise makes listening to the desired signal easier and more comfortable for the wearer. This reduction of out-of-band noise also increases intelligibility of the desired input sounds (e.g., speech or other desired sounds) for the wearer.

Figure 8A:
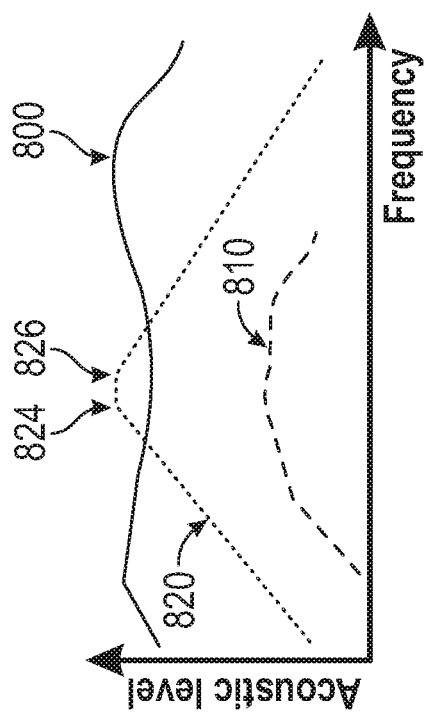
FIG. 8A is a graph showing acoustic level versus frequency for voice partially masked by noise, wideband background noise, and a filter operation according to an embodiment.
Figure 8B:
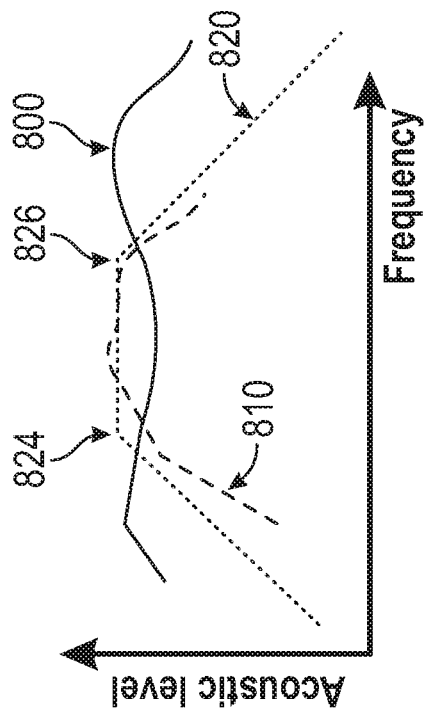
FIG. 8B is a graph showing acoustic level versus frequency for voice partially masked by noise, wideband background noise, and a filter operation according to an embodiment.
Figure 8C:
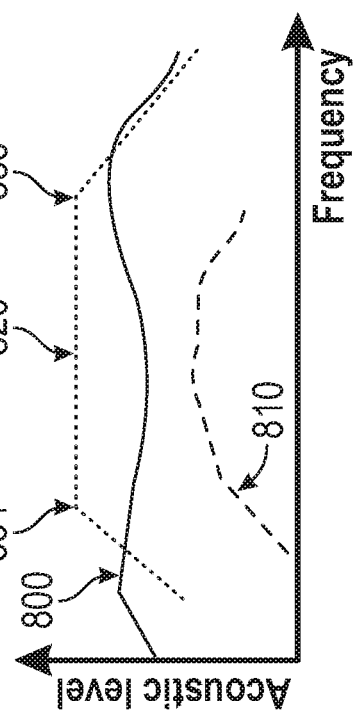
FIG. 8C is a graph showing acoustic level versus frequency for voice partially masked by noise, wideband background noise, and a filter operation according to an embodiment.
Figure 8D:
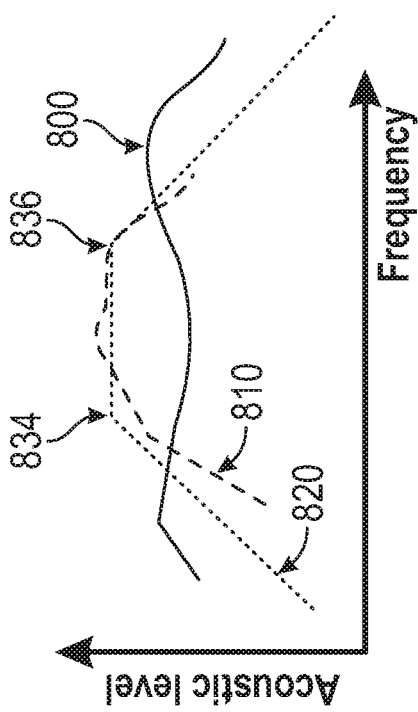
FIG. 8D is a graph showing acoustic level versus frequency for voice partially masked by noise, wideband background noise, and a filter operation according to an embodiment.
Figure 8F:
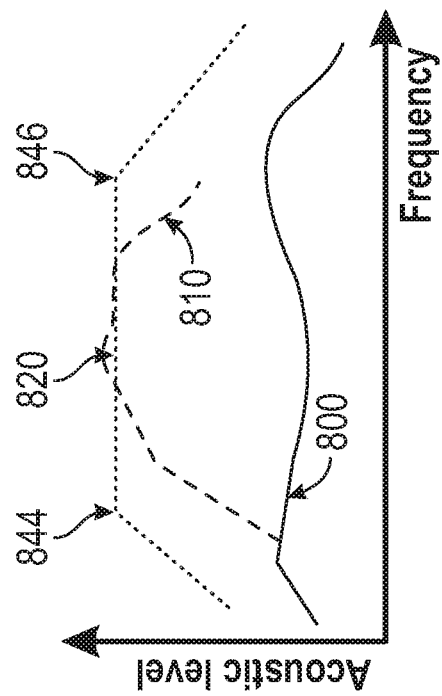
FIG. 8F is a graph showing acoustic level versus frequency for voice partially masked by noise, wideband background noise, and a filter operation according to an embodiment.
Figure 8E:
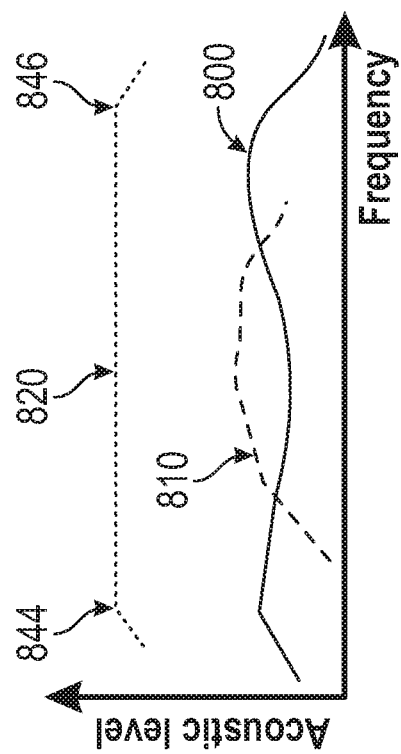
FIG. 8E is a graph showing acoustic level versus frequency for voice partially masked by noise, wideband background noise, and filter operation according to an embodiment.

FIGS. 8A-8F demonstrate the adaptive surround sound filter and how it can be adjusted for desired signals despite various levels of voice and background noise. The filter can be adjusted based on both the detected characteristics of voice signal and background noise, such that the adaptive system can be made to respond differently to various noise and voice environments. FIGS. 8A-8F show the output level on the vertical axis and the frequency of the output on the horizontal axis for each environment. The filter (or combination of filters) can be focused around desirable frequencies, such as a range of frequencies that includes human voices. As shown in FIGS. 8A-8E, the filter(s) (e.g., as shown in FIG. 8E) can focus on a wider range of frequencies in a low level noise environment than the filter(s) in a high noise environment (shown in FIG. 8A).

FIGS. 8A & 8B show high amplitude or level noise environments with either relatively low voice levels 810 (FIG. 8A) or relatively high voice levels (FIG. 8B), which are partially masked by the wideband background noise 800 yet which are still detectable by the VAD. Once voice is detected, the filter 820 of the system is adjusted to widen the pass band to highlight signals within the spectrum of interest (e.g., the voice spectrum). The widening of the pass band can ensure the voice remains intelligible despite a relative disparity between the intensity of the background noise and the voice signal or absolute high levels of sound.

FIGS. 8A & 8B show a representation of a band pass filter (or combination of high pass and low pass filters) applied when the level of the noise is above a first selected threshold and the level of voice is above or below a selected threshold. The filter can filter out frequencies below the first low frequency 824 and above the first high frequency 826. The frequencies between the first low frequency 824 and the first high frequency 826 can include the common frequencies for human voices. The filter in FIG. 8A can includes more narrow range (difference between the low frequency and high frequency points) than the filter in FIG. 8B, to concentrate on common frequencies for human voices in a particularly loud noise environment. The low and high frequencies can change over time as conversation or other human voice output is detected.

FIGS. 8C & 8D show an environment featuring medium noise levels with either relatively low level voice signals 810 (FIG. 8C) or relatively high level voice signals (FIG. 8D), each of which are partially masked by the wideband background noise 800 yet which are still detectable by the VAD. Depending on, for example, a confidence value assigned to the signals detected by the VAD, the filter 820 is adjusted to widen or narrow the pass band to highlight signals within the spectrum of interest. In FIGS. 8C & 8D, the pass band is narrowed as the voice level is increased.

FIGS. 8C & 8D include a representation of a band pass filter (or combination of high and low pass filters) applied when the level of background noise is below the first selected threshold and the level of voice is above or below a second selected threshold. The band pass filter(s) can filter out frequencies below the second low frequency 834 and above the second high frequency 836. The frequencies between the low frequency 834 and the high frequency 836 can include the common frequencies for human voices. The band pass filter(s) can have a wider range than the filter(s) operating in FIG. 8A.

FIGS. 8E & 8F show an environment featuring low noise levels with either relatively low level voice signals 810 (FIG. 8C) or relatively high level voice signals (FIG. 8D), each of which are partially masked by the wideband background noise 800 yet which are still detectable by the VAD. The filter 820 is again adjusted to widen or narrow the pass band to highlight signals within the spectrum of interest. In FIGS. 8D & 8E, the pass band is narrowed as the voice level is increased.

FIGS. 8E & 8F include a representation of a band pass filter (or combination of high and low pass filters) applied when the level of background noise is below both the first selected threshold and second selected noise threshold, and the level of voice is above or below a selected voice threshold. The filter(s) can filter out frequencies below the third low frequency 844 and above the third high frequency 846. The third s filter(s) can have a wider range (difference between the low frequency and high frequency points) than the filter(s) operating in FIGS. 8A-8D.

The second high frequency can be greater or equal to the first high frequency. The third high frequency can be greater or equal to the second high frequency. The second low frequency can be less than or equal to the first low frequency. The third low frequency can be less than or equal to the second low frequency. The first low frequency and the first high frequency can be within the range of the second low frequency to the second high frequency. The second low frequency and the second high frequency can be within the range of the third low frequency to the third high frequency. The combination of band pass filters being applied is selected from a group of band pass filters including one or more band pass filters, such as two band pass filters, three band pass filters, four band pass filters, five band pass filters, or six band pass filters. In various embodiments, a band pass filter can include a high pass filter in series with a low pass filter.

In various embodiments, the adaptive systems described herein may include rate limiters associated with any of the components. Such rate limiters may be configured to allow the system to: 1) account for and identify the voice soon after the detection of signals within the voice spectrum by the VAD; and 2) continue attenuating background noise for a pre-determined period after the VAD ceases to detect voice signals. The rate limiters can thus be configured to give precedence to sampling voice over noise by limiting a rate of change in the attenuation state of the filter (or combination of filters), thereby allowing the system to quickly adjust for voice when a conversation is started, stay in voice state during short pauses in conversation and revert slowly after conversation has ended. This prevents the wearer from experiencing abrupt transitions in noise level during use.

In various embodiments, the cups of the headwear are cushioned and have a cushioned cut away for improved gun stock clearance and damage prevention.

In one embodiment, the hearing protector provides for noise protection based on the environment, e.g., based on gunshot noise, as well as for noise selection, e.g., voice noise to improve speech intelligence. In one embodiment, the hearing protector is formed of materials that are lightweight, e.g., which allows for extended wear. In one embodiment, the hearing protector is formed of or covered by material that is comfortable, thereby allowing for comfortable, extended wear. In one embodiment, the hearing protector includes a headband that is adjustable, e.g., allowing for hats or caps to be worn with the headwear. In one embodiment, the headwear includes a vented headband, which provides for improved ventilation, reduces pressure points and/or improves comfort. In one embodiment, the headwear can be folded, thereby providing for more compact storage. In one embodiment, a storage bag is provided. In one embodiment, the storage bag is adapted to hold the folded headwear. In one embodiment, the storage bag is adapted to hold disassembled headwear, e.g., a headband that is separate from the rest of or other parts of the headwear, such as the ear cups.

In one embodiment, the headwear includes sealing rings, such as those formed of or covered by a soft material, e.g., leather, which provide for improved fit and comfort. In one embodiment, the headwear includes an audio jack, e.g., for MP3 and 2-way radio compatibility.

Embodiments

1. An adaptive hearing protection system, comprising: right and left microphones providing input signals; and a peak detector in communication with an adjustable amplifier to sense high amplitude sounds and attenuate gain of the adjustable amplifier, the peak detector further in communication with a low pass filter that controllably filters signals from the adjustable amplifier, wherein the peak detector includes an adjustable threshold for comparisons of the input signals, the peak detector further configured to provide adjustable attenuation based on input energy of the input signals.

2. The adaptive hearing protection system of embodiment 1, further comprising: a voice activity detector in communication with a high pass filter to control a high pass cutoff of the high pass filter, the high pass filter disposed between the adjustable amplifier and the low pass filter; and a frequency spectrum analyzer in communication with a notch filter, the notch filter disposed between the high pass filter and the low pass filter.

3. The adaptive hearing protection system of embodiment 1, wherein the peak detector is configured to adjust attenuation based on an input energy threshold.

4. The adaptive hearing protection system of embodiment 1, further comprising: a voice activity detector in communication with a high pass filter to control a high pass cutoff of the high pass filter, the high pass filter disposed between the adjustable amplifier and the low pass filter.

5. The adaptive hearing protection system of embodiment 1, wherein, on sensing of a high amplitude sound, the gain of the adjustable amplifier is attenuated to keep peaks in the high amplitude sound below an adjusted threshold level.

6. The adaptive hearing protection system of any of the preceding embodiments, wherein the high amplitude sound includes gunshots and echoes.

7. The adaptive hearing protection system of embodiment 1, wherein the peak detector is further configured to increase the duration of attenuation as the input energy of the input signals increases relative to an adjusted threshold.

8. The adaptive hearing protection system of embodiments 1 or 7, wherein the peak detector is further configured to decrease the duration of attenuation as the input energy of the input signals decreases relative to an adjusted threshold.

9. The adaptive hearing protection system of embodiment 1, wherein the adjustable threshold of the peak detector is adjusted in inverse relation to the input energy of the input signals.

10. The adaptive hearing protection system of embodiment 2 or 4, wherein the voice activity detector is configured to detect input signals within a first frequency spectrum, the frequency spectrum analyzer is configured to detect wideband noise, and wherein the high pass filter and low pass filter are configured to attenuate wideband noise outside the first frequency spectrum.

11. The adaptive hearing protection system of embodiment 2, wherein the voice activity detector is configured to detect input signals within a first frequency spectrum, the frequency spectrum analyzer is configured to detect narrowband noise, and wherein the notch filter is configured to attenuate the narrowband noise within the first frequency spectrum.

12. The adaptive hearing protection system of embodiments 10, wherein the low pass filter is configured to attenuate below a first frequency, wherein the high pass filter is configured to attenuate above a second frequency, and wherein the first and second frequencies are adjustable based on at least one of the input energy of the input signals and an output signal from the voice activity detector.

13. The adaptive hearing protection system of embodiment 12, wherein, in use, the difference between the first and second frequencies is increased upon detection of a noise level above a select noise threshold and an output signal indicative of voice signals above a select voice threshold.

14. The adaptive hearing protection system of embodiment 12, wherein, in use, the difference between the first and second frequencies is decreased upon detection of noise levels above a noise threshold and an output signal indicative of voice signals below a select voice threshold.

15. A method for highlighting voice signals in a high noise environment, the method comprising; detecting voice signals in a frequency spectrum of interest; detecting a noise level associated with a background noise signal; selecting one or more filters defining a band with a first cutoff frequency and a second cutoff frequency; modifying the width of the band based at least partially on the detected noise level; and attenuating the noise signal below the first cutoff frequency and above the second cutoff frequency.

16. The method of embodiment 14, and further comprising detecting an acoustic voice level, and wherein modifying the width of the band is based partially on the voice level.

17. The method of embodiment 15, wherein modifying the width of the band comprises increasing the width of the band when the detected noise level is above a selected noise threshold.

18. The method of embodiment 15, wherein modifying the width of the band comprises narrowing the width of the band when the detected noise level is below a selected noise threshold.

19. The method of embodiment 16, wherein modifying the width of the band comprises narrowing the width of the band when the detected noise level is above a selected noise threshold and the detected voice level is below a voice threshold.

20. The method of embodiment 19, wherein modifying the width of the band comprises increasing the width of the band when the detected noise level is above a selected noise threshold and the detected voice level is above a voice threshold.

21. The method of embodiment 19, wherein modifying the width of the band comprises narrowing the width of the band when the detected noise level is above a selected noise threshold and the detected voice level is above a voice threshold.

22. The method of embodiment 15, and further comprising detecting a lack of a voice signal in the frequency spectrum of interest and continuing to attenuate the noise signal for a predetermined period of time after the lack of a voice signal has been detected.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this present disclosure pertains. All publications and patent applications are herein incorporated by reference to the same extent as if each individual publication or patent application was specifically and individually indicated by reference.

The present disclosure has been described with reference to various specific and preferred embodiments and techniques. However, it should be understood that many variations and modifications may be made while remaining within the spirit and scope of the present disclosure.

The invention claimed is:

1. An adaptive hearing protection system, comprising:
   right and left microphones providing input signals; and
   a peak detector in communication with an adjustable amplifier to sense high amplitude sounds and attenuate gain of the adjustable amplifier, the peak detector further in communication with a low pass filter that controllably filters signals from the adjustable amplifier; and
   a voice activity detector in communication with a high pass filter to control a high pass cutoff of the high pass filter, the high pass filter disposed between the adjustable amplifier and the low pass filter,
   wherein the peak detector includes an adjustable threshold for comparisons of the input signals, the peak detector further configured to provide adjustable attenuation based on input energy of the input signals.

2. The adaptive hearing protection system of claim 1, further comprising
   a frequency spectrum analyzer in communication with a notch filter, the notch filter disposed between the high pass filter and the low pass filter.

3. The adaptive hearing protection system of claim 2, wherein the voice activity detector is configured to detect input signals within a first frequency spectrum, the frequency spectrum analyzer is configured to detect wideband noise, and wherein the high pass filter and low pass filter are configured to attenuate wideband noise outside the first frequency spectrum.

4. The adaptive hearing protection system of claim 3, wherein the low pass filter is configured to attenuate below a first frequency, wherein the high pass filter is configured to attenuate above a second frequency, and wherein the first and second frequencies are adjustable based on at least one of the input energy of the input signals and an output signal from the voice activity detector.

5. The adaptive hearing protection system of claim 4, wherein, in use, the difference between the first and second frequencies is at least one of,
   increased upon detection of a noise level above a select noise threshold and an output signal indicative of voice signals above a select voice threshold, and
   decreased upon detection of noise levels above a noise threshold and an output signal indicative of voice signals below a select voice threshold.

6. The adaptive hearing protection system of claim 2, wherein the voice activity detector is configured to detect input signals within a first frequency spectrum, the frequency spectrum analyzer is configured to detect narrowband noise, and wherein the notch filter is configured to attenuate the narrowband noise within the first frequency spectrum.

7. The adaptive hearing protection system of claim 1, wherein the peak detector is configured to adjust attenuation based on an input energy threshold.

8. The adaptive hearing protection system of claim 1, wherein, on sensing of a high amplitude sound, the gain of the adjustable amplifier is attenuated to keep peaks in the high amplitude sound below an adjusted threshold level.

9. The adaptive hearing protection system of claim 1, wherein the high amplitude sound includes at least one of gunshots and echoes.

10. The adaptive hearing protection system of claim 1, wherein the peak detector is further configured to increase the duration of attenuation as the input energy of the input signals increases relative to an adjusted threshold.

11. The adaptive hearing protection system of claim 10, wherein the peak detector is further configured to decrease the duration of attenuation as the input energy of the input signals decreases relative to an adjusted threshold.

12. The adaptive hearing protection system of claim 1, wherein the peak detector is further configured to decrease the duration of attenuation as the input energy of the input signals decreases relative to an adjusted threshold.

13. The adaptive hearing protection system of claim 1, wherein the adjustable threshold of the peak detector is adjusted in inverse relation to the input energy of the input signals.

14. A method for highlighting voice signals in a high noise environment, the method comprising;
   detecting voice signals in a frequency spectrum of interest;
   detecting a noise level associated with a background noise signal;
   selecting one or more filters defining a band with a first cutoff frequency and a second cutoff frequency;
   modifying the width of the band based at least partially on the detected noise level;
   and attenuating the noise signal below the first cutoff frequency and above the second cutoff frequency,
   wherein modifying the width of the band comprises one of increasing the width of the band when the detected noise level is above a selected noise threshold and the detected voice level is above a voice threshold and narrowing the width of the band when the detected noise level is above a selected noise threshold and the detected voice level is above a voice threshold.

15. The method of claim 14, and further comprising detecting an acoustic voice level, and wherein modifying the width of the band is based partially on the voice level.

16. The method of claim 14, wherein modifying the width of the band comprises one of increasing the width of the band when the detected noise level is above a selected noise threshold and narrowing the width of the band when the detected noise level is below a selected noise threshold.

17. The method of claim 14, wherein modifying the width of the band comprises narrowing the width of the band when the detected noise level is above a selected noise threshold and the detected voice level is below a voice threshold.

18. The method of claim 14, and further comprising detecting a lack of a voice signal in the frequency spectrum of interest and continuing to attenuate the noise signal for a predetermined period of time after the lack of a voice signal has been detected.

19. An adaptive hearing protection system, comprising:
   right and left microphones providing input signals; and a peak detector in communication with an adjustable amplifier to sense high amplitude sounds and attenuate gain of the adjustable amplifier, the peak detector further in communication with a low pass filter that controllably filters signals from the adjustable amplifier, wherein the peak detector includes an adjustable threshold for comparisons of the input signals, the peak detector further configured to provide adjustable attenuation based on input energy of the input signals, and wherein the adjustable threshold of the peak detector is adjusted in inverse relation to the input energy of the input signals.

\* \* \* \* \*